United States Patent [19]

Freed

[11] Patent Number: 5,480,644

[45] Date of Patent: Jan. 2, 1996

[54] USE OF INJECTABLE BIOMATERIALS FOR THE REPAIR AND AUGMENTATION OF THE ANAL SPHINCTERS

[75] Inventor: Jeffrey S. Freed, New York, N.Y.

[73] Assignee: JSF Consultants Ltd., New York, N.Y.

[21] Appl. No.: 843,124

[22] Filed: Feb. 28, 1992

[51] Int. Cl.$^6$ .............................. A61F 2/02; A61K 38/39; C07K 15/20

[52] U.S. Cl. .......................... 424/436; 514/801; 514/882; 523/113; 523/121; 525/54.1; 530/356

[58] Field of Search ..................................... 424/423, 436, 424/465, 484; 514/801, 2, 12, 21, 882; 530/350, 353, 356, 399; 435/273; 525/54.1; 523/113, 115, 121; 524/415, 417

[56] References Cited

U.S. PATENT DOCUMENTS

| | | | |
|---|---|---|---|
| 2,696,456 | 4/1950 | Hetterick | 424/436 |
| 3,197,369 | 7/1965 | Widmann et al. | 424/436 |
| 3,650,275 | 3/1972 | Von der Mozel | 128/407 |
| 3,749,100 | 7/1973 | Von der Mozel | 128/407 |
| 3,949,073 | 4/1976 | Daniels | 424/177 |
| 3,952,726 | 4/1976 | Hennig | 128/1 R |
| 4,209,009 | 6/1980 | Hennig | 128/1 R |
| 4,401,107 | 8/1983 | Haber | 128/1 R |
| 4,424,208 | 1/1984 | Wallace | 424/177 |
| 4,582,640 | 4/1986 | Smestad | 260/123.7 |
| 4,686,985 | 8/1987 | Lottick | 128/344 |
| 4,760,131 | 7/1988 | Sundsmo | 530/356 |
| 4,781,176 | 11/1988 | Ravo | 600/30 |
| 4,803,075 | 2/1989 | Wallace | 424/423 |
| 4,904,256 | 2/1990 | Yamaguchi | 623/14 |
| 4,950,483 | 8/1990 | Ksander | 424/422 |
| 4,969,902 | 11/1990 | Ravo | 623/12 |

OTHER PUBLICATIONS

U.S. Ser. No. 06/619,028, inventor: O'Connor, "Method Of Improving The Competency Of Defective Sphincters," Filed Jun. 11, 1984 and abandoned on Aug. 27, 1985.

K. W. O'Connor, MD, and G. A. Lehman, MD, (1988) "Endoscopic placement of collagen at the lower esophageal sphincter to inhibit gastroesophageal reflux: a pilot study of 10 medically intractable patients," *Gastrointestinal Endoscopy*, 34(2):106–112.

Linda M. Dairiki Shortliffe, Fuad S. Freiha, Robert Kessler, Thomas A. Stamey, and Christos E. Constantinou, (Mar. 1989) "Treatment of Urinary Incontinence By The Periurethral Implantation Of Glutaraldehyde Cross–Linked Collagen," *The Journal of Urology*, 141:538–541.

*Primary Examiner*—Carlos A. Azpuru
*Attorney, Agent, or Firm*—Townsend & Townsend & Crew

[57] ABSTRACT

This invention discloses methods of repairing structurally defective or inadequately functioning muscles of the anal sphincter and methods of improving the competency of incompetent anal sphincters by administering an effective amount of an injectable biomaterial into the defect or into the anal sinuses. Preferred biomaterials to be used in this invention are collagen formulations.

13 Claims, No Drawings

USE OF INJECTABLE BIOMATERIALS FOR THE REPAIR AND AUGMENTATION OF THE ANAL SPHINCTERS

TECHNICAL FIELD

This invention is in the field of medical implants and prostheses. More particularly, it concerns a nonsurgical technique for repairing structurally defective or inadequately functioning anal sphincters and for improving the competency of anal sphincters by injecting biomaterials into the defect or into the anal sinuses.

BACKGROUND OF THE INVENTION

Anal sphincters are muscular structures that assist in controlling the flow of body wastes (feces and flatus) from the colon. The internal anal sphincter (IAS) and the external anal sphincter (EAS) encircle the anal canal and comprise the anorectal ring. The IAS is a thickening of the gastrointestinal smooth muscle; it maintains continence at rest. The EAS is composed of striated, voluntary muscle. The EAS, the puborectalis, and the levator ani muscles work in concert to prevent leakage of flatus and feces when there is an increase in abdominal pressure or when the internal anal sphincter relaxes after rectal distention.

When one or both sphincters become defective or incompetent, the control of feces and/or flatus is impaired. Incontinence of the feces and flatus is socially and psychologically disabling for the afflicted patient. It is a major factor prejudicing the rehabilitation and placement prospects of the elderly and disabled, preventing many of them from being cared for at home.

The normal mechanisms of anorectal continence include the motor function of the anal sphincters and pelvic floor muscles, the role of the rectum and sigmoid colon as a fecal reservoir with capacitance and compliance and as a propulsive force with intrinsic motor activity, the effects of stool consistency, volume and delivery rate, the anorectal angle, and anorectal sensation. It is the coordinated integration of these factors that confers continence.

There are two distinct etiologies for anorectal incontinence. The most common cause of anorectal incontinence is a structural deformity due to anatomic disruption of the sphincter mechanism, which may be caused by obstetric injuries (perineal laceration and improperly performed median episiotomies), complications of fistula or fissure surgery (keyhole deformities), traumatic injuries (e.g., impalement injuries), or cancer. Alternatively, anorectal incontinence may result from deterioration of the sphincter muscles due to age, congenital disorders, systemic and metabolic diseases, acquired neurological defects, and diseases of the colon and rectum.

Present treatment modalities for anorectal incontinence include nonsurgical and surgical therapy. Nonsurgical therapy for incontinence must be tailored to each individual: patients suffering from urgency incontinence may benefit from the use of bulk-forming agents and laxatives or enemas; individuals with minor degrees of incontinence may find biofeedback and perineal strengthening exercises beneficial in alleviating symptoms of seepage and occasional loss of control.

Current nonsurgical treatments for anorectal incontinence include the use of electrical stimulation to improve contraction of the sphincter muscles and the use of anorectal plugs which are designed to expand post-insertion.

U.S. Pat. Nos. 3,650,275 and 3,749,100 describe an electrostimulation device to maintain contraction of the sphincter muscle. A magnetic artificial anus closing device is described in U.S. Pat. No. 3,952,726. U.S. Pat. No. 4,209,009 discloses an anus closure tampon with nonhomogeneous sections having differential diametrical compressibility to provide a plug effect. U.S. Pat. No. 4,401,107 describes an intestinal control valve arranged to surround the anal-terminating descending intestine, thereby functioning as an artificial sphincter. A device comprising three inflatable chambers (the first, positioned outside the rectum; the second, within the anal sphincter muscle; the third, outside the body between the buttocks) to maintain anal continence is disclosed in U.S. Pat. No. 4,686,985. U.S. Pat. Nos. 4,781,176 and 4,969,902 teach an artificial anus comprising a hollow tubular support member and a releasable plug for sealing closed the support member. A pressure transducer or electrical contact is provided on the support member and connected to an electrode in contact with the patient's skin, so that when the colon becomes pressurized the patient is signalled that the plug should be released. U.S. Pat. No. 4,904,256 describes a magnetic artificial anus assembly, having a sphincter function similar to the natural anus, which comprises an annular bag structure filled with a magnetic fluid and a plug structure having a magnet member.

Surgical therapy must also be individualized, and is directed either at (i) repair of the disrupted sphincter or (ii) augmentation (with autogenic transplanted muscle or commercially available Silastic sheet prostheses) of existing structures to improve physiologic function. Diverting colostomy is rarely necessary.

Unfortunately, there are inherent difficulties and risks in these corrective methods. For example, anorectal plugs will often cause infection, fibrosis of the mucosa, or muscularis of the bowel near the plug. Also, patients complain about the discomfort and inconvenience of temporary plugs that function similar to absorbent pads. An artificial sphincter may extrude or malfunction, necessitating additional surgery or corrective action. Surgery also can result in infection or other complications, such as host-graft rejection, and is a significant expense. Therefore, it is desirable to treat anal sphincter deficiencies on a cost-effective, outpatient basis, such that the inherent difficulties presented by the current methods are avoided.

Injectable biomaterials, e.g., Polytef® paste (polytetrafluoride, Mentor), injectable liquid silicone, and collagen, have been used to augment incompetent lower esophageal sphincters and urinary sphincters over the past ten years. These so-called sphincters, however, are not true sphincteric muscles because they are controlled by pressure changes, rather than neurological stimulation from the brain. Furthermore, the use of injectable biomaterials for treating lower esophageal and urinary sphincters is simply to bulk up the surrounding tissue by injecting the biomaterial to close the respective orifice.

SUMMARY OF THE INVENTION

In contrast to the lower esophageal and urinary sphincters, the anal sphincters are highly vascular and muscular areas with involuntary contracture by the IAS and voluntary contracture by the EAS mechanisms. If either of these sphincters is rendered incompetent due to any of the previously described causes, varying degrees of anorectal incontinence may be the result. One aspect of this invention is a method for repairing or replacing structurally defective or inadequately functioning muscles of the anal sphincters by administering an effective amount of an injectable biomaterial perianally into the defect or structural deformity. The invention further includes a method for improving the competency of incompetent anal sphincters by administering an effective amount of an injectable biomaterial into the anal sinuses between the blood vessels. Another aspect of the invention is a method of inducing wound healing of a structurally defective anal sphincter by administering an effective amount of an injectable biomaterial containing one or more wound healing agents, such as a biologically active protein growth factor, into the defect. In some instances, the biomaterial, particularly when it is a collagen material, may create a fibrolytic bridge between the ends of the sphincter.

A method for repairing defective or incompetent anal sphincter muscles ideally would include a nonsurgical procedure utilizing biocompatible materials that are non-immunogenic, have a low risk for infection, and are easy to administer. The present invention provides such an effective method for repairing defective or incompetent anal sphincter muscles by administering an injectable biocompatible biomaterial.

DETAILED DESCRIPTION OF THE INVENTION

The invention is a method for repairing structurally defective or inadequately functioning muscles of the anal sphincters by perianally administering an effective amount of an injectable biomaterial(s), with and without wound healing agents, into the defect or structural deformity. The invention further comprises a method for improving the competency of incompetent anal sphincters by administering injectable biomaterials into the anal sinuses between the blood vessels. Improvement of the sphincter's competence will improve fecal and flatus continence and increase the anorectal squeeze pressure, resulting in improved control.

The term "incompetent," as used herein, refers to sphincter muscles that are inadequately functioning or nonfunctioning due to the deterioration of the sphincter muscles or due to a structural deformity caused by anatomic disruption of the sphincter mechanism.

The term "improving the competency," as used herein, means augmenting the existing sphincter muscle to improve the patient's baseline continence level. Improved competence would result in increased resting squeeze pressure, maximal squeeze pressure, and threshold volume as can be measured by standard manometric tests. An alternative method for measuring improved competence is by a change in clinical grading from major incontinence to minor incontinence to continence. Major incontinence occurs when there is deficient control or lack of control of stool of normal consistency. Minor incontinence is a disorder in which there is partial soiling or occasional incontinence of flatus or of loose or watery stools. Continence is when there is no soiling or occasional incontinence due to flatus or loose or watery stools.

The term "effective amount" as used herein, means the quantity of biomaterial needed to repair anal sphincter muscle or to achieve improved competence as measured by standard manometry or the quantity of wound healing agents needed to achieve improved healing. The effective amount of biomaterial administered may vary depending on the patient's own ability to absorb or break down the biomaterial, the consistency and concentration of the material, and the site and condition being treated. Furthermore, the biomaterial may be administered over a number of treatment sessions to achieve and maintain improved competence as measured by standard manometry.

The biomaterial used in the invention may be selected from a number of sources; however, it must be injectable, biocompatible, essentially non-immunogenic, and persist at the site of placement for at least three months. Alternatively, the biomaterial may be an aqueous suspension of a biopolymer with a biocompatible fluid lubricant to improve the intrusion of the biopolymer into the tissue. See U.S. Pat. No. 4,803,075, which is incorporated herein by reference. Commercially available suspensions of a biopolymer and fluid lubricant may be obtained from Bioplasty, Inc. (Minneapolis, Minn.) under the tradename Bioplastique Micro-Implants. Fluid lubricants may include: hyaluronic acid, dextran sulfate, dextran, succinylated non-crosslinked collagen, methylated non-crosslinked collagen, glycogen, glycerol, dextrose, maltose, triglycerides of fatty acids, egg yolk phospholipids, heparin, and the like. Biopolymers may include: atelopeptide fibrillar, crosslinked or non-crosslinked collagen, gelatin beads, polytetrafluoroethylene beads, silicone rubber beads, hydrogel beads, silicon carbide beads, glass beads, and the like.

A preferred biomaterial comprises a collagen formulation. Most preferred are those collagen formulations wherein the collagen is atelopeptide fibrillar, crosslinked, or non-crosslinked collagen, or collagen mixed with a mineral material. Collagen is a major protein component of bone, cartilage, skin, and connective tissue in animals. Collagen in its native form is typically a rigid, rod-shaped molecule approximately 300 nanometers (nm) long and 1.5 nm in diameter. It is composed of three collagen polypeptides which form a tight triple helix. The collagen polypeptides are characterized by a long midsection having the repeating sequence —Gly—X—Y—, where X and Y are often proline or hydroxyproline, bounded at each end by the "telopeptide" regions, which constitute less than about 5 percent (%) of the molecule. The telopeptide region of the collagen chains are typically responsible for the crosslinking between chains and for the immunogenicity of the protein. Collagen occurs in types, of varying physical properties; the most abundant are Types I–III.

The collagen used in the invention may be collected from any number of mammalian sources, such as bovine or porcine corium and human placenta. The preparation of purified, substantially nonantigenic collagen in solution from the skin is basically a three-step process involving solubilization, enzyme treatment, and purification. See U.S. Pat. Nos. 4,140,537 and 4,488,911; which are incorporated herein by reference. The term "collagen" or "collagen material" as used herein refers to all forms of collagen, including those which have been processed or otherwise modified.

Preferred collagens are treated to remove the immunogenic telopeptide regions ("atelopeptide collagen"), are soluble, and will have been reconstituted into the fibrillar form ("atelopeptide fibrillar"). The reconstituted fibrillar collagen may optionally be crosslinked using methods generally known in the art, such as by heat, radiation, or chemical crosslinking agents. Commercially reconstituted collagens are available under the tradenames Zyderm Collagen Implant and Zyplast Collagen Implant (Collagen Corporation, Palo Alto, Calif.). See U.S. Pat. Nos. 4,582,640 and 3,949,073; which are incorporated herein by reference.

U.S. Pat. No. 4,424,208; incorporated herein by reference, discloses an improved collagen formulation suitable for use in soft tissue augmentation. The formulation comprises reconstituted fibrillar atelopeptide collagen in combination with particulate, crosslinked atelopeptide collagen dispersed in an aqueous medium. The addition of particulate crosslinked collagen improves the biomaterial's persistence, or ability to resist shrinkage following injection.

U.S. Pat. No. 4,557,764; incorporated herein by reference, discloses a "second nucleation" collagen precipitate which exhibits a desirable malleability and putty-like consistency. Collagen is provided in solution [e.g., at 2–4 milligrams per milliliter (mg/ml)], and a "first nucleation product" is precipitated by rapid titration and centrifugation. The remaining supernatant (containing the bulk of the original collagen) is then decanted and allowed to stand overnight. The precipitated second nucleation product is collected by centrifugation.

Copending U.S. patent application Ser. No. 07/433,441; pending incorporated herein by reference, discloses an improved injectable collagen formulation which is conjugated to a chemically activated polymer, such as polyethylene glycol. The conjugated collagen has improved persistence at the implantation site. Also disclosed in the pending application is a method for crosslinking the collagen material with a bifunctional-activated polymer in situ, such as polyethylene glycol. This improved process method allows the collagen implant to be crosslinked to the host tissue by the activated polymer.

Another embodiment of the biomaterial to be used in the invention includes a high collagen concentration formulation, which is disclosed in U.S. patent application Ser. No. 07/843,770, filed Feb. 28, 1992; abandoned incorporated herein by reference. Briefly, collagen in solution (Vitrogen 100 Collagen, Celtrix Laboratories, Palo Alto, Calif.) is reconstituted to fibril form by neutralizing the solution with the addition of a phosphate buffer at ambient temperatures. The resultant fibrillar collagen may be optionally crosslinked using standard techniques known in the art prior to concentration. The high concentration collagen materials disclosed herein are passed through a homogenizer (HC5000, Microfluidics Corporation, Newton, Mass.) to improve the extrudability of the material through a fine gauge needle. High concentrations of non-crosslinked and crosslinked fibrillar collagen are expected to have improved persistence compared to commercially available forms.

Another particularly useful biomaterial to be used in the disclosed invention is described in U.S. patent application Ser. No. 07/843,646, filed Feb. 28, 1992; abandoned (Attorney Number 05921-11) incorporated herein by reference, which describes an injectable collagen/ceramic formulation. Briefly, porous and/or non-porous ceramic particles are prepared to have a uniform particle size distribution in the range of about 50–250 microns. The preferred ceramic particles are admixed with fibrillar collagen to produce an injectable ceramic/collagen formulation. The addition of the ceramic particles improves the persistence of the injectable collagen formulation.

Other commercially available biomaterials useful in the described invention are a polytetrafluoride (Teflon) paste, known as Polytef Paste, and a porcine collagen particulate suspended in saline, known as Fibrel Gelatin Matrix Implant (both available from Mentor Corporation, Santa Barbara, Calif.). Further biomaterials include fluid suspensions containing: gelatin beads, glass beads, hydrogel beads, silicone rubber or carbide beads, polytetrafluoride beads, and the like.

An effective amount of wound healing agents may be added to the biomaterial used in the invention to improve long-term restoration of the sphincter defect. These agents include protein growth factors such as fibroblast growth factors (FGFs), platelet derived growth factors (PDGFs), epidermal growth factors (EGFs), connective tissue activated peptides (CTAPs), transforming growth factors (TGFs), and the like. These biologically active agents are known to facilitate regrowth of connective tissue cells and accumulation of fibroblasts, endothelial cells, and wound healing regulatory cells to speed wound healing. One or more of these agents in combination can be used in the invention. The amount of wound healing agent(s) to be included with the biomaterial may vary, depending upon the biomaterial used, the patient (age, sex, medical history) and the site being treated. Typically the weight ratio of wound healing agent(s) to the biomaterial would be in the range of about 1:5,000 to 1:50,000.

The wound healing agents may be isolated from native or natural sources, such as from mammalian cells, or may be prepared synthetically, such as by recombinant DNA or by chemical processes. In addition, analogs, fragments, or derivatives of these agents may be used, provided they exhibit some of the biological activity or wound healing properties of the native molecule. For example, analogs can be prepared by expression of genes altered by site-specific mutagenesis or other genetic engineering techniques.

These agents may be added to the biomaterial during preparation or just prior to treatment. It is preferred that the wound healing agents be incorporated into the biomaterial such that the agents are released through a sustained delivery. In this way, the agents can be released over an extended period of time into the anal sphincter sites and surrounding areas, promoting wound healing. It is most preferred that these agents will be included in the patient's treatment in those instances where the biomaterial is being used to repair the anal sphincter muscles.

Optionally, antimicrobial additives and/or antibodies may be added to these biomaterials to reduce the potential for infection at the treatment site. In addition, local anesthetics may be used at the injection site. Any appropriate additive may be utilized as long as it is compatible with the biomaterial used and the patient.

A preferred method of the invention is performed in an outpatient setting under aseptic conditions with the patient in the lithotomy position. A retractor is used to clearly visualize the anal orifice and the biomaterial is typically supplied in a sterile 3.0 cubic centimeters (cc) syringe fitted with a 25 gauge needle.

An anorectal examination is preferably conducted prior to treatment. The examination includes direct visualization of the lower rectum and anal canal, as well as palpation of the perianal area and anorectal ring. An anoscope (a metal device approximately three inches in length) will be used to visualize the tissues of the anal canal and lower rectum; the sphincter mass and function will be assessed by palpation of the sphincter mechanism while the patient is asked to strain and squeeze. Pre-examination preparation is not required (i.e., Fleet enema) and the examination is of minimal duration (1–2 minutes).

When repairing structurally defective sphincters, such as a keyhole deformity resulting from surgery or trauma, the biomaterial, optimally containing wound healing agents, is injected perianally into the deformity, using one or more injections, until the physician observes that the treated area has been restored to its original form and the defect is repaired (i.e., the hole or defect is no longer visible to the skilled physician). The patient's continence level is then measured using standard manometry.

The process of evaluating anal continence is divided into two areas: subjective reporting of the patient's symptoms and objective measurement of the change in anal sphincter pressure.

A scale has been created to measure change in patients' reporting of their symptoms. The data being measured includes complaints of itching, bleeding, difficulty or ease of evacuation, nocturnal sleep disturbance, staining of undergarments, prolapse of tissue, and need for other forms of therapy. Typically the scale is as follows (based upon degree of complaint): 1+=minimal complaint, 2+=moderate, 3+=severe, and 4+=incapacitating.

Objective data is obtained through the use of anal manometry. Manometry, by measurement of pressure, supplies information about muscle activity at the time of actual measurement. Baseline continence levels are measured both prior to and following treatment. Anal manometric evaluation helps to define the results of improved continence based upon the pressures obtained pre- and post-treatment. The apparatus used typically comprises a four-channel radially perfused balloon-tipped catheter, pressure transducers, and a multichannel recorder. The following are measured and are recorded on the appropriate medical record: resting squeeze pressure, maximal squeeze pressure, anorectal reflex, and threshold volume. Although anal manometry will show variations during the course of the day, measuring basal and opening pressures before and after injection in the same patient will allow for determination of the efficacy of the technique on increasing anal sphincter pressure. Each patient will therefore act as his/her own control.

To improve, restore, and/or supplement the competency of the incompetent sphincters, the biomaterial is injected into the submucosa of the anal sinuses. It is important that the biomaterial is not injected into the blood vessels, as this may cause vascular occlusion, infarction, or embolic phenomena. A preferred amount of biomaterial to be used in the repair of structural defects varies from patient to patient, however, is about between 1–40 cc.

A preferred amount of biomaterial to be used is about between 15–40 cc, most preferably about 20–30 cc for augmentation of the anal sphincters; whereas about 5–10 cc of biomaterial may be used in muscle repair. The amount of material necessary to effect repair of structural defects or restoration of competency will, of course, vary with the degree of tissue loss or destruction to the area. Alternatively, the treating physician may wish to augment treatment for repairing structurally defective sphincters by injecting the biomaterial, optionally containing wound healing agent(s), into the submucosa of the anal sinuses, before or after perianal injection of the biomaterial into the defect or structural deformity. Then the patient's continence level is measured using standard manometry. Successful treatment is also defined in terms of the patient's report of a decrease in incontinent episodes.

Improvements in continence and repair of damaged tissue is expected to last a minimum of about 3 to 6 months. The injections may optionally be repeated on a regular basis to maintain continence and correction of damaged tissue. It is expected that subsequent injections will require less material than the initial treatment.

Methods for repairing structurally defective or inadequately functioning muscles of the anal sphincters may be conducted by perianally administering an injectable biomaterial, with or without wound healing agents, into the structural deformity. Also disclosed are methods for improving the competency of the anal sphincter by administering an injectable biomaterial into the anal sinuses. These methods provide nonsurgical approaches for treating anorectal incontinence.

The following experimental section is offered by way of example and not by limitation. The invention is described below in some detail for the purposes of clarity and understanding. It will be apparent, however, that certain changes and modifications may be practiced within the scope of the appended claims.

EXPERIMENTAL

A patient presented a complaint of anal leakage secondary to a posterior anal (keyhole) deformity which was secondary to excision of a fissure several years before. Local care failed to control the symptoms of anal leakage and, approximately three months later, a sphincteroplasty and loop sigmoid colostomy were performed. About two months later closure of the colostomy was accomplished and the patient remained continent for about six months. Due to the marked scarring in the area of the anal sphincter surgery, the repair slowly failed and within ten months of the colostomy closure, the patient again had marked anal leakage.

Because of the patient's refusal to undergo further surgery, a decision was made to "bolster" the defect and enhance the sphincter function with an injection of commercially available atelopeptide fibrillar collagen. Twenty cc of collagen was injected into the defect and surrounding tissues without any analgesia or anesthesia in an outpatient setting. For six months the patient remained completely continent without any symptoms. At that point, signs and symptoms of anal leakage developed.

What is claimed is:

1. A method of improving the competency of incompetent anal sphincters comprising (1) selecting an injectable biomaterial capable of persisting at a site of its injection for at least three months, and (2) injecting an effective amount of the injectable material into the anal sinuses between the blood vessels, sufficient to improve competency of the incompetent anal sphincter.

2. The method of claim 1, wherein said injectable biomaterial comprises atelopeptide fibrillar, crosslinked or non-crosslinked collagen.

3. The method of claim 1, wherein said injectable biomaterial is an aqueous suspension of a material selected from the group consisting of atelopeptide fibrillar, crosslinked collagen, non-crosslinked collagen, gelatin beads, polytetrafluoroethylene beads, silicone rubber beads, hydrogen beads, silicon carbide beads and glass beads, with a biocompatible fluid lubricant.

4. The method of claim 3 wherein said biocompatible fluid lubricant is selected from the group consisting of: hyaluronic acid, dextran sulfate, dextran, succinylated non-crosslinked collagen, methylated non-crosslinked collagen, glycogen, glycerol, dextrose, maltose, triglycerides of fatty acids, egg yolk phospholipids, and heparin.

5. The method of claim 1, wherein said injectable biomaterial is a second nucleation collagen.

6. The method of claim 2 wherein said collagen is conjugated to a chemically activated polymer.

7. The method of claim 6 wherein said chemically activated polymer is polyethylene glycol.

8. The method of claim 2 wherein said collagen is crosslinked with a bifunctional activated polymer.

9. The method of claim 8 wherein said collagen and said bifunctional activated polymer crosslink in situ.

10. The method of claim 8 wherein said bifunctional activated polymer is polyethylene glycol.

11. The method of claim 2 wherein said biomaterial further comprises a ceramic and/or mineral material.

12. The method of claim 11 wherein said ceramic material comprises ceramic particles in the size range of about 50–250 microns.

13. The method of claim 1 wherein said biomaterial further comprises an antimicrobial additive and/or antibiotic.

* * * * *